(12) United States Patent
Li et al.

(10) Patent No.: US 9,768,888 B2
(45) Date of Patent: Sep. 19, 2017

(54) INTEGRATED PASSIVE AND WIRELESS SENSOR

(71) Applicant: King Abdullah University of Science and Technology, Thuwal (SA)

(72) Inventors: Bodong Li, Thuwal (SA); Jürgen Kosel, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 387 days.

(21) Appl. No.: 14/528,448

(22) Filed: Oct. 30, 2014

(65) Prior Publication Data

US 2015/0117157 A1    Apr. 30, 2015

Related U.S. Application Data

(60) Provisional application No. 61/897,948, filed on Oct. 31, 2013.

(51) Int. Cl.
  *H03H 9/25*    (2006.01)
  *H01L 41/107*  (2006.01)
  (Continued)

(52) U.S. Cl.
  CPC ............ *H04B 11/00* (2013.01); *G01K 1/00* (2013.01); *G01K 11/265* (2013.01);
  (Continued)

(58) Field of Classification Search
  CPC . G01L 23/10; G01L 1/16; G01L 9/008; G01L 9/2233; G06G 7/195; H04B 11/00; G01K 1/00; G01K 11/265; G01N 29/041; G01R 33/09; G01R 33/093; G01R 33/098; H03H 9/25
  (Continued)

(56) References Cited

U.S. PATENT DOCUMENTS 4,343,688 A * 8/1982 Harwood ............ G01N 27/121
                                                     204/430
5,739,416 A * 4/1998 Hoenk ................. G01N 25/68
                                                     324/664

(Continued)

FOREIGN PATENT DOCUMENTS

CN    102095687 B * 5/2012  ............... G12N 2/17

*Primary Examiner* — Thomas Dougherty
(74) *Attorney, Agent, or Firm* — Thomas | Horstemeyer, LLP

(57) ABSTRACT

A passive and wireless sensor is provided for sensing at least one of magnetic field, temperature or humidity. The sensor can provide only one of the sensing functions, individually or any combination of them simultaneously. It can be used for various applications where magnetic field changes, temperature and/or humidity need to be measured. In one or more embodiments, a surface acoustic wave (SAW) sensor is provided that can measure one or more of a magnetic field (or current that generates the magnetic field), temperature and humidity. In one or more embodiments, a magnetoimpedance (MI) sensor (for example a thin film giant magnetoimpedance (GMI) sensor), a thermally sensitive (for example a Lithium Niobite ($LiNbO_3$)) substrate, and a humidity sensitive film (for example a hydrogel film) can be used as sensing elements.

18 Claims, 6 Drawing Sheets

(51) Int. Cl.
*H04B 11/00* (2006.01)
*G01K 1/00* (2006.01)
*G01R 33/09* (2006.01)
*G01N 29/04* (2006.01)
*G01K 11/26* (2006.01)

(52) U.S. Cl.
CPC ............ *G01N 29/041* (2013.01); *G01R 33/09* (2013.01); *G01R 33/093* (2013.01); *G01R 33/098* (2013.01); *G01N 2291/02845* (2013.01); *G01N 2291/0423* (2013.01)

(58) Field of Classification Search
USPC ...... 310/313 R, 313 A–313 D, 317–319, 338
See application file for complete search history.

(56) References Cited

U.S. PATENT DOCUMENTS

| | | | | |
|---|---|---|---|---|
| 6,293,136 B1* | 9/2001 | Kim | ................... | G01N 29/022 310/313 B |
| 7,750,420 B2* | 7/2010 | Field | ................... | H03H 3/0073 257/414 |
| 8,669,871 B2* | 3/2014 | Malocha | ............ | G06K 19/0672 340/5.7 |
| 9,106,205 B2* | 8/2015 | Gallagher | .............. | H03H 9/642 |
| 2007/0064765 A1* | 3/2007 | Solie | ....................... | G01K 1/024 374/117 |
| 2007/0283758 A1* | 12/2007 | Funo | ....................... | G01H 17/00 73/570 |
| 2009/0109048 A1* | 4/2009 | Spivak | ................... | H03K 17/94 340/686.6 |
| 2009/0206844 A1* | 8/2009 | Sabah | .................... | G01N 29/02 324/636 |
| 2012/0068573 A1* | 3/2012 | Obata | ................. | H03H 9/02551 310/313 A |
| 2013/0130362 A1* | 5/2013 | Hines | .................... | G01N 29/024 435/287.1 |
| 2013/0139599 A1* | 6/2013 | Lee | ....................... | G01N 29/022 73/602 |
| 2014/0253094 A1* | 9/2014 | M'Jahed | ................ | G01R 23/02 324/76.39 |
| 2015/0000399 A1* | 1/2015 | Lee | .................... | G01C 19/5698 73/504.01 |
| 2015/0260587 A1* | 9/2015 | Zheng | .................. | G01K 11/265 374/117 |

* cited by examiner

GMI + $r_3$ $r_{1-3}$

INTEGRATED PASSIVE AND WIRELESS SENSOR

CROSS REFERENCE TO RELATED APPLICATIONS

This application claims priority to and the benefit of U.S. provisional application entitled "INTEGRATED PASSIVE AND WIRELESS SENSOR" having Ser. No. 61/897,948, filed Oct. 31, 2013, which is hereby incorporated by reference in its entirety.

CROSS-REFERENCE TO RELATED DOCUMENTS

This application makes reference to and incorporates by reference the following paper as if it were fully set forth herein expressly in its entirety:

B. Li, O. Yassine and J. Kosel, "Integrated passive and wireless sensor for magnetic fields, temperature and humidity" (attached hereto as Appendix A).

TECHNICAL FIELD

The present disclosure generally relates to a passive and wireless sensor device, in particular for the sensing of magnetic field, temperature and/or humidity.

BACKGROUND

In many sensor applications, monitoring of different parameters is necessary, which typically requires employment of different sensors at the same time. This not only increases the complexity of the task but also increases the number of wires for communication. For example, in high voltage transmission line monitoring, in addition to current sensing, wire temperature and environmental humidity sensing are also important, providing critical information for maintaining high safety standards. The conventional approach employs a radio system that consists of multiple sensors directly connected to a wireless communication module and an energy source [7]. The conventional approach suffers from a number of disadvantages, including but not limited to, the large amount of wiring required, the problems with operating in harsh environments, and the difficulty in providing an energy source.

Accordingly, there is a need to address the aforementioned deficiencies and inadequacies.

SUMMARY

The present disclosure provides a passive and wireless sensor for sensing at least one of magnetic field, temperature or humidity. The sensor can provide only one of the sensing functions, individually or any combination of them simultaneously. It can be used for various applications where magnetic field changes, temperature and/or humidity need to be measured.

The present disclosure provides remote data collection using a novel, passive, wireless sensor device design. This device has the ability to collect data by detecting changes in the magnetic field in its immediate vicinity. In addition, the device can sense and relay information regarding the temperature and/or humidity of its immediate vicinity. In various aspects the device is designed to sense only one of the parameters. In various other aspects, the device is designed to sense any combination or all three parameters thus providing a comprehensive picture of the operational environment where it is located. Each of these three parameters is detected by a separate sensing element. The simple design allows the device to include only one, two or all three of the sensing elements in a measurement.

The present device provides a number of unique capabilities. For example, it can gather data without the need for batteries or other power sources, and it can transmit the data wirelessly, for example to a nearby transceiver. These aspects reduce the complexity of mounting the sensor at the desired location (e.g., overhead transmission lines to monitor electrical current flow, line temperature and environment humidity). Additionally, the construction of the device is such that it provides good sensitivity without having delays or interferences between the various signals being transmitted and received by the device.

Traditional sensors currently used do not offer the advantages to the same degree as present disclosure. Either multiple sensors are required to monitor different parameters, or a large amount of additional wiring is required, or a radio transmitter module and energy source like battery needs to be included [13]. Advantages of the present device include its ability to measure the magnetic field, temperature and/or humidity in harsh environments and places where wiring is not feasible. Other physical quantities correlated to magnetic fields can also be measured using the present sensor. These include for example current flow in a conductor, stress in a magnetic material, structure change of a magnetic material and distance to a magnetic material.

The present device uses wireless and passive SAW (Surface Acoustic Wave) technology to do the monitoring. This is a benefit since SAW devices are effective in performing continuous measurements of logistical, physical, mechanical, and electrical parameters without the need for on-chip power or wires. SAW transponders in sensor devices are able to overcome environmental reflection issues and can operate reliably in harsh indoor-outdoor environments [14]. Wireless and passive sensors provide ideal solutions for such applications. They significantly reduce the safety risk caused by wiring and maintenance.

In one or more embodiments, a surface acoustic wave (SAW) sensor is provided that can measure one or more of a magnetic field (or current that generates the magnetic field), temperature and humidity. In embodiments any combination of the three or all three can be measured simultaneously. It can be used as a multifunctional transmission line monitoring sensor. In one or more embodiments, a magnetoimpedence (MI) sensor (for example a thin film giant magnetoimpedance (GMI) sensor), a thermally sensitive (for example a Lithium Niobite ($LiNbO_3$)) substrate, and a humidity sensitive film (for example a hydrogel film) can be used as sensing elements.

After being excited, at least one SAW transponder is modified during propagation and reflection in terms of magnitude and phase, the modification representing the measurand. For example, the measurand can be a measure of a change in any one or more of humidity, magnetic field or temperature. If several transponders are used, there is interference between different sensing signals, which is taken into consideration in the design.

In one or more embodiments the sensor comprises: at least one input transducer for receiving a signal and generating surface acoustic waves from the signal; and at least one surface acoustic wave propagation path for receiving a surface acoustic wave from the input transducer, the at least one surface acoustic wave propagation path including a reflector transducer coupled with or operating as a sensor, wherein the sensor is selected from the group consisting of a humidity sensor, a magnetic field sensor, a temperature sensor, and combinations thereof. In one or more embodiments, the sensor can comprise at least two surface acoustic wave paths for receiving a surface acoustic wave from the input transducer, one of the two surface acoustic wave paths including a reflector transducer coupled with a humidity sensor, and another of the at least two surface acoustic wave propagation paths including at least one of a reflector transducer coupled with a magnetic field sensor or a reflector transducer operating as a temperature sensor, the one and the another of the at least two surface acoustic wave propagation paths being protected against influencing each other.

In one or more embodiments, a method is provided for sensing a change in one or more measurands, comprising the steps of: receiving a signal and generating surface acoustic waves from the signal; propagating a surface acoustic wave along at least one surface acoustic wave propagation path, the at least one surface acoustic wave propagation path including a reflector transducer sensor coupled with or operating as a sensor, wherein the sensor is selected from the group consisting of a humidity sensor, a magnetic field sensor a temperature sensor, and combinations thereof; reflecting the surface acoustic wave propagated along the at least one surface acoustic wave path; and determining a phase shift or an amplitude change or both in the surface acoustic wave reflected in the at least one of the surface acoustic wave propagation paths thereby sensing a change in at least one of humidly, magnetic field or temperature as a measurand. In one or more embodiments, the surface acoustic waves are propagated along at least two surface acoustic wave paths, one of the at least two surface acoustic wave propagation paths including a reflector transducer and a humidity sensor coupled with the humidity sensor, and another of the at least two surface acoustic wave propagation paths including at least one of a reflector transducer coupled with a magnetic field sensor or a reflector transducer operating as a temperature sensor, the method further comprising reflecting the surface acoustic waves propagated along the at least two surface acoustic wave paths, and protecting the one and the another of the at least two surface acoustic wave paths against influencing each other.

In any one or more embodiments, the sensor and the method for sensing are realized by integrating a surface acoustic wave (SAW) transponder with a magneto-impedance (MI) sensor and a delay line coated with a humidity sensitive hydrogel. The device can be made on a thermally sensitive substrate. For example, the device can be made on a Lithium Niobite substrate and may utilize two SAWs, which are generated at two input inter-digital transducers (IDTs) and reflected at multiple, for example three, reflector IDTs. The delay line between the input and a first IDT (IDT1) is coated with the humidity sensitive hydrogel. Therefore, a phase shift or amplitude change or both are obtained when the humidity changes. The waves reflected at a second IDT (IDT2) are used to determine temperature changes, as well as compensate the temperature influence on the humidity signal by the phase shift or amplitude change or both of the reflected signals. In various aspects, the MI sensor is connected to a third IDT (IDT3). The MI sensor changes its impedance upon changes of a magnetic field, which in turn changes the reflected signal of the load IDT. As shown below, the sensor is characterized using a network analyzer under changing conditions of all three physical parameters.

In one or more embodiments an entire product may consist of a transceiver with a transceiver antenna and the present sensor device with a sensor antenna.

The sensor is characterized using a network analyzer and wire connection through an RF cable. A simultaneous current and temperature measurement was also carried out using this sensor on a current line.

Other systems, methods, features, and advantages of the present disclosure for our passive and wireless sensor and method of sensing, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Described below are various embodiments of the present systems and methods for our passive and wireless sensor. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

The present disclosure provides passive and wireless sensing solutions for magnetic field, temperature and/or humidity. In an embodiment it can be realized on a single chip. The device can provide only one of the above mentioned sensing functions or any combination of them. It can be applied in different applications including for example transmission line monitoring, car and traffic monitoring, construction monitoring and health monitoring.

In one or more embodiments, the present device can be used for transmission line monitoring. The so-called "smart gird" is an electrical grid that utilizes information and communication technology to monitor and optimize the efficiency, reliability and sustainability of electricity production and distribution. It has become an important topic in the global energy development. In a smart grid system, real-time current and voltage monitoring at the grid nodes are essential as they provide key information for the real-time current organization and scheduling strategy. Magnetic sensors have been widely used for current sensing in transmission lines. The task of transmission line monitoring requires, in addition to the current measurement, sensing of wire temperature and environmental humidity as these parameters provide critical information for maintaining high safety standards. Wireless and passive sensors provide ideal solutions for such applications, as they significantly reduce the safety risk caused by wiring and maintenance.

Figure 1:
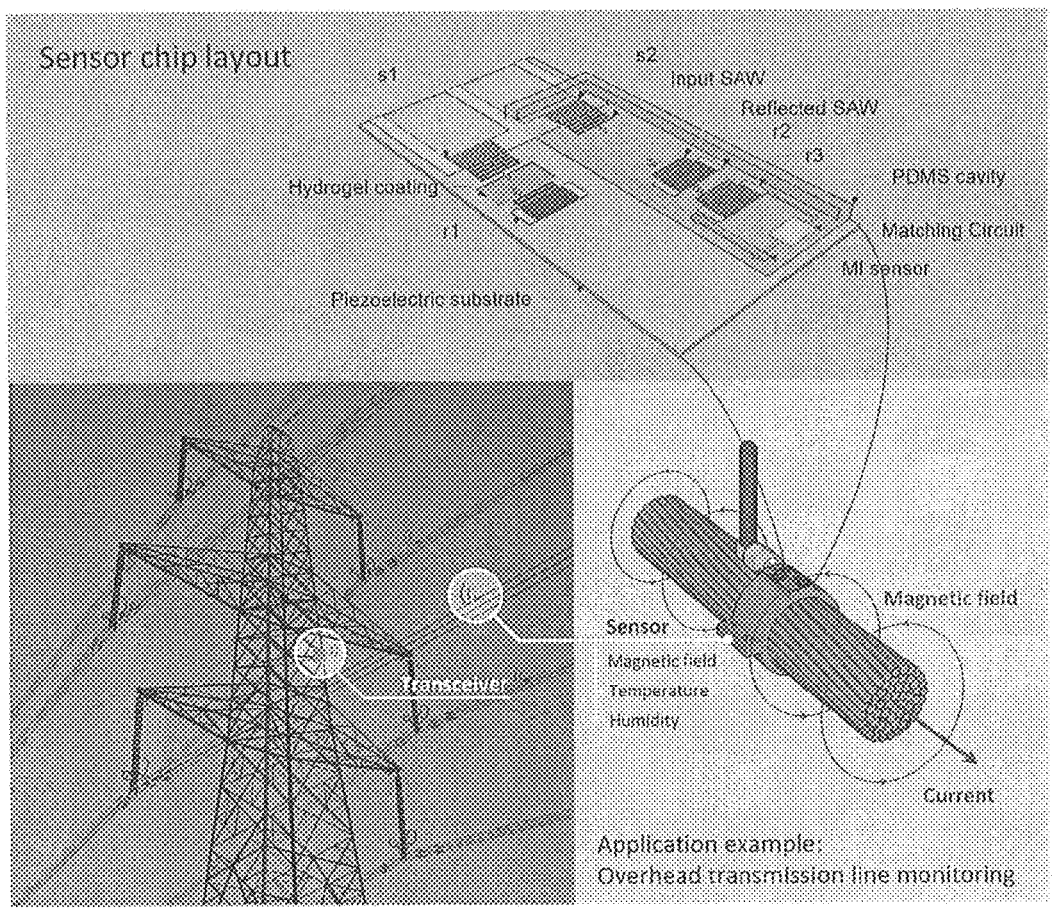
FIG. 1 depicts use of an exemplary embodiment of the present sensor in overhead transmission line monitoring.

The present disclosure is suitable for the above application and can provide a simultaneous measurement of current, wire temperature and/or environmental humidity on multiple spots of the transmission lines without wiring and maintenance. For example, as illustrated in FIG. 1 the device can be attached to the transmission line and detect these parameters passively and wirelessly (current sensing through magnetic field) via a transceiver close by. No battery and no maintenance are required, making the device a good candidate for such harsh and dangerous application.

In one or more embodiments, the present device can be used for car and traffic detection. In intelligent transportation systems, car detection has recently emerged as an important application for wireless magnetic sensors. Based on the detection of the earth magnetic field's distortion caused by a car, magnetic sensors are explored for traffic monitoring, vehicle counting, speed monitoring, as well as vehicle classification. Compared to traditional techniques such as ultrasonic, infrared and optical sensing, magnetic field solutions are less environmentally dependent providing advantages in dark, snowy, rainy and foggy weather conditions. Battery based wireless magnetic sensors have been commercialized and installed in the roadbed for collecting car parking information.

The present disclosure provides a solution for above applications by using a passive wireless multifunctional sensor. It can sense the car and, if needed, temperature and humidity which provides information for both traffic and road condition. Thereby, it does not require a battery or wire connection and can be interrogated from a distance, where a transceiver can be conveniently placed and operated in conjunction with the sensor.

For example, the presence or absence of a car can be detected with a magnetic field sensor through the measurement of the earth magnetic field distortion. In a parking monitoring application, the sensor can be installed on or, in the ground in the parking lots and provide important information for the drivers to find empty parking lots. In the traffic monitoring application, the sensor can be installed on or in the road, providing traffic information such as car speed, traffic density or type of car through the magnetic field measurement. The temperature and humidity data collected by the sensor provides road condition information, which is important from a safety point of view and could provide valuable information for drivers and traffic control departments. Thus, applications for the present device include traffic monitoring and parking lot occupancy detection. The integrated thin film based single chip design reduces the size, complexity and cost of the sensor, making it suitable for mass production and easy installation in the roadbed. It is worth to point out that no maintenance is required once it is installed.

In the field of passive and wireless sensing techniques, surface acoustic wave (SAW) sensors have attracted great interest in the past decades [1-3]. Different from silicon-based wireless sensing modules, SAW sensors are small, maintenance free, identifiable and cheap. Based on the piezoelectric effect, by converting the wireless signal into vibrational energy and coupling with different sensing mechanisms, a number of SAW-based sensors have been developed to measure a variety of physical and chemical parameters. These sensors have also been shown to be suitable for measurements at poorly accessible locations such as closed chambers, rotating motor shafts, underground, etc. [4-6].

In general, in an embodiment the present SAW-based passive wireless sensing system consists of three major components: 1) a wireless transmitter, which sends out a burst of high frequency signals; 2) a SAW sensor, which receives and reflects modified signals based on the physical quantity being measured; and 3) a receiver, which captures the codified signals. The transmitter and receiver can be combined as a transceiver or interrogator.

In one or more embodiments, the sensor device is a single function sensor device that includes an input transducer, for example an input inter-digital transducer, for receiving a signal and generating surface acoustic waves from the signal, and at least one surface acoustic wave propagation path for receiving a surface acoustic wave from the input transducer, the at least one surface acoustic wave propagation path including a reflector transducer coupled with or operating as a sensor. The sensor can be a humidity sensor, a magnetic field sensor, or a temperature sensor.

In one or more embodiments the sensor device of the present disclosure can be a multi-function sensor device. For example it can be composed of a surface acoustic wave (SAW) transponder with a magneto-impedance (MI) sensor and a delay line coated with a humidity sensitive material. The device can be made on a piezoelectric substrate (e.g., Lithium Niobate LiNbO3). The device may utilize a plurality of SAW transponders, for example two SAW transponders. One or more input inter-digital transducers (IDTs) may be used to receive an input signal. Surface acoustic waves (SAWs) can be generated at the one or more input inter-digital transducers (IDTs). For example, if two SAW transponders are employed SAWs may each be generated at a corresponding input IDT, s1 and s2. The generated SAWs can be reflected at reflector IDTs. In a non-limiting example three reflector IDTs may be employed, r1, r2 and r3, one for each of the three types of sensors.

The device may work as a delay line type SAW transponder. For example, a delay line can be provided between a first input inter-digital transducer s1 and a first reflector inter-digital transducer r1 and coated with a humidity sensitive material such as a hydrogel. Examples of suitable humidity sensitive materials include $TiO_2$, ZnO, hematoporphyrin (Hp), polyphenylacetylene (PPA), poly-(distibutyl-phosphine)-platinum-diethynylbiphenyl (Pt-DEPB), poly-(distibutylphosphine)-palladium-diethynylbiphenyl (Pd-DEPB), polyethynylfluorenol (PEFL) and other hydrogel and polymers both as continuous films or nanostructures such as nanowires and nanodots.

A phase shift or amplitude change or both of the reflected signal is obtained, when the humidity changes. Thus, the surface acoustic waves reflected at the first reflector inter-digital transducer r1 can be used to determine humidity changes by the phase shift or amplitude change or both of the reflected signal at the first reflector inter-digital transducer r1. The waves reflected at a second input inter-digital transducer s2 can be used to determine temperature changes by the phase shift or amplitude change or both of the reflected signals at a second reflector inter-digital transducer r2. The MI sensor can be connected to a third reflector inter-digital transducer r3, and changes its impedance upon changes of a magnetic field, which in turn changes the reflected signal from r3. The magneto-impedance (MI) sensor can be a thin film MI sensor composed of one or more conducting layers and soft magnetic layers with different geometries such as stripes, meanders with different dimensions. The MI sensor can also contain one or more antiferromagnetic layers. Discrete or on-chip matching components (inductors, capacitors) may be used to connect between the MI sensor and its associated reflector IDT.

The present sensor device requires no battery or wiring. It can be wirelessly interrogated using a transceiver. Multiple sensors within the reading distance of the transceiver can be interrogated simultaneously. Thus, the presented device can be used for sensing one or more of magnetic field, temperature and humidity, for example, in harsh environments or in places where wiring is not feasible or undesirable. Other physical quantities correlated to magnetic fields such as current flow in a conductor, stress in a magnetic material and/or distance to a magnetic material can also be measured using the present sensor.

Figure 2:
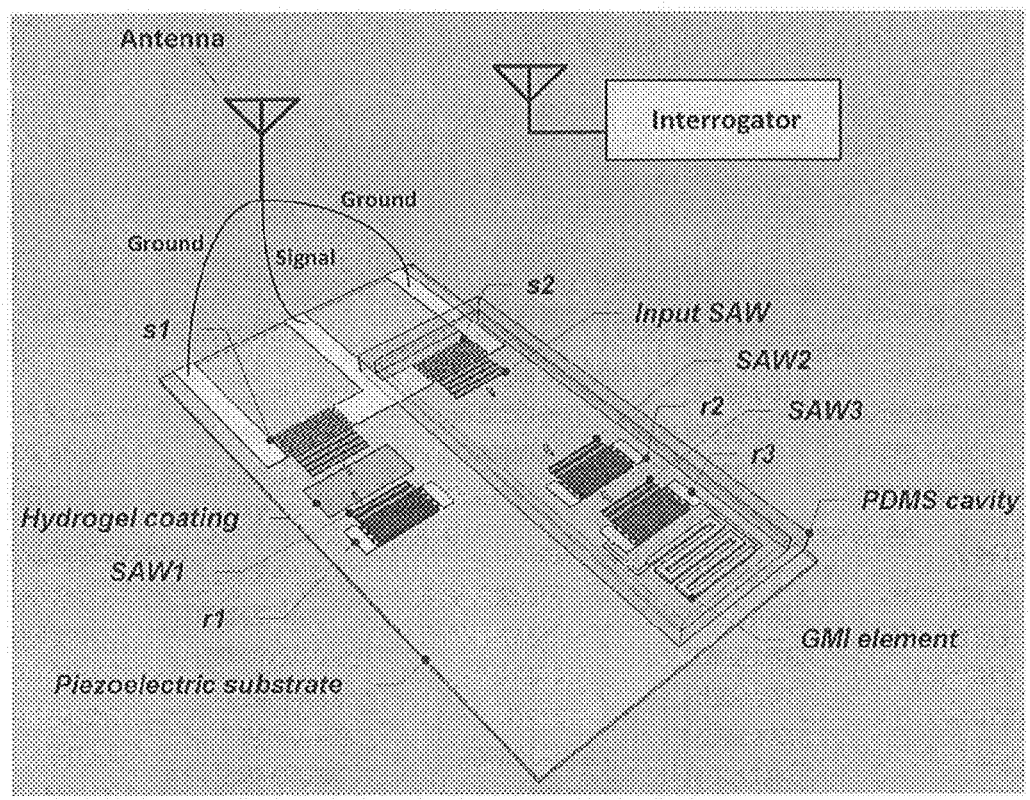
FIG. 2 depicts a schematic of a non-limiting example of the present sensor.
Figure 3A:
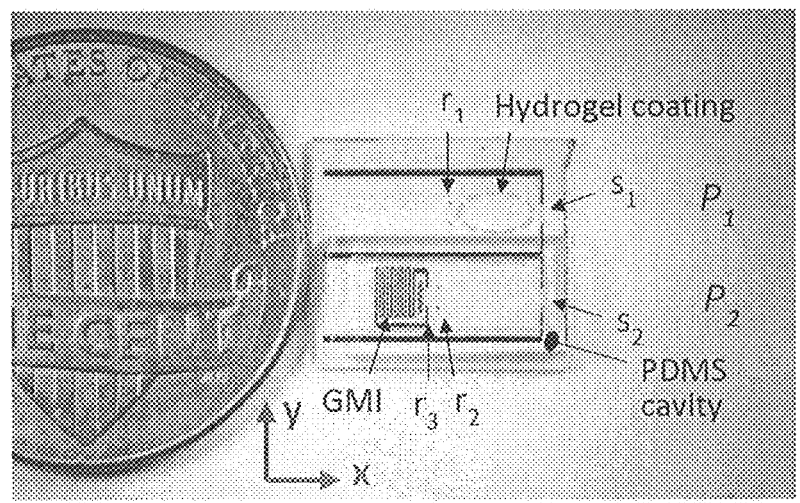
FIG. 3(a) depicts an exemplary fabricated sensor.
Figure 3B:
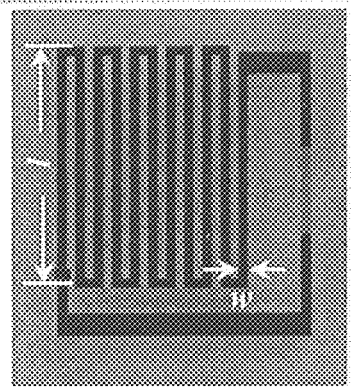
FIG. 3(b) depicts an exemplary giant magneto-impedance (GMI) sensor and associated reflector inter-digital transducer (IDT).
Figure 3C:
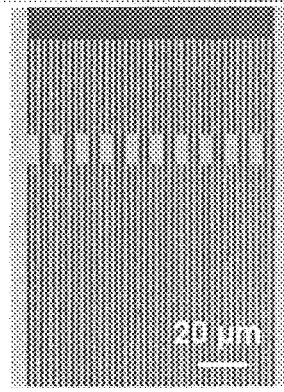
FIG. 3(c) depicts an exemplary reflector IDT.

FIGS. 2 and 3 depict an exemplary schematic of an embodiment of the system including a multi-functional sensor. A transceiver communicates wirelessly with the sensor via one or more antennas, for example a pair of antennas. On the sensor substrate (for example, a piezoelectric substrate), two bi-directional inter-digital transducers (IDT), $s_1$ and $s_2$, are provided to receive a signal from the antenna(s) and are connected in parallel to create at least two surface acoustic wave (SAW) propagation paths, $P_1$ and $P_2$ (FIG. 3(a)), though the sensor can be designed to include only one of the surface acoustic wave paths. Three split-finger inter-digital transducers (IDTs) serve as reflectors for the three different sensing parameters, for example as illustrated in FIG. 3(c). Reflector $r_1$ is placed on path $P_1$, which is coated with a hydrogel layer between $r_1$ and $s_1$ for humidity measurements. The other two reflectors, $r_2$ and $r_3$, are placed on path $P_2$, where $r_3$ is connected to a GMI element for magnetic field measurements, and $r_2$ works as a reference for both $r_1$ and $r_3$ and, at the same time, as a temperature sensor. A polydimethylsiloxane (PDMS) cavity is mounted on top of path $P_2$ to protect it from humidity influence. The design of paths $P_1$ and $P_2$ takes into account mounting of the PDMS cavity to protect reflectors $r_2$ and $r_3$ without blocking the SAW path for reflector $r_1$.

Surface acoustic waves (SAWs) are generated at input inter-digital transducers $s_1$ and $s_2$ when the excitation frequency matches the resonant frequency f of the IDT. The resonant frequency is defined by the acoustic velocity v of the substrate and the wavelength $\lambda$ or electrode period p of the IDTs through $f=v/\lambda=v/p$. When input inter-digital transducers $s_1$ and $s_2$ are excited, the SAWs are generated and propagate along paths $P_1$ and $P_2$ to the reflectors. The reflected SAWs (SAW$_1$ reflected at $r_1$, SAW$_2$ at $r_2$ and SAW$_3$ at $r_3$) propagate back to input inter-digital transducers $s_1$ and $s_2$ carrying the sensing information in their amplitude and phase change. In detail, SAW$_1$ contains humidity and temperature information, SAW$_2$ is only influenced by the temperature and SAW$_3$ carries both magnetic field and temperature information. By comparing amplitude and phase of SAW$_1$, SAW$_2$ and SAW$_3$, all three sensing parameters can be extracted, as described for example below.

In various embodiments, the number of electrode pairs can be 10 for both source (input) and reflector IDTs, though other numbers of electrode pairs can be used. In an embodiment, the sensor can be designed at 433 MHz, which corresponds to an electrode period p=9 μm. The electrode width w can then be 1.13 μm for reflector IDT's $r_1$, $r_2$, $r_3$ and 2.25 μm for source (input) IDT's $s_1$ and $s_2$. The aperture of the input and reflector IDT electrodes is 690 μm.

A. Magnetic Field Sensor

In any one or more of various embodiments, the magnetic field measurement can be based on the attenuation of the reflected signal SAW$_3$, due to the impedance change of the load at reflector $r_3$, which is a GMI sensor, when a magnetic field is applied. The GMI effect is the impedance change of an ac-powered ferromagnetic conductor upon the change of a magnetic field. It originates from the skin effect in conjunction with a change of the complex permeability [8]. As an example, in the presented SAW sensor, a meander structured tri-layer GMI sensor can be used, which consists of a copper (Cu) conducting layer, sandwiched by two $Ni_{80}Fe_{20}$ magnetic layers. This geometry provides a large GMI effect and involves a fairly simple fabrication process [9]. In general, the impedance value of a GMI sensor is governed by the applied magnetic field and operating frequency, which can be expressed as Z=Z(H, f). In the case of a SAW integrated device, the operation frequency of the GMI sensor is the same as the resonant frequency of the associated input and reflector IDTs.

According to the P-matrix model [10], the acoustic reflectivity $P_{11}$ of a reflector IDT is correlated with its impedance load, in this case, Z(H, f). Thus, the acoustic reflectivity of the reflector $r_3$ can be expressed as $P_{11}$(H, f). Its real and imaginary parts represent the amplitude and phase of SAW$_3$, respectively. The change of $P_{11}$ can be evaluated by measuring the electrical reflection coefficient at the input port of the source IDTs. Previous work on a SAW magnetic field sensor has shown a 2.7 dB amplitude change and 20° phase shift of the resonant peak of the caused by magnetic field changes [11] Due to the fact that the attenuation depends not only on the losses from the reflector but also on other losses during the wireless transmission, an open circuited reflector $r_2$ can be used to provide an amplitude reference for reflector $r_3$. Therefore, the magnetic field signal of the sensor can be expressed as $$S_m = \text{amp}(SAW_3 - SAW_2)(dB), \quad (1)$$

where amp(SAW$_i$), i=2, 3, refers to the amplitude value of $S_{11}$ corresponding to SAW$_i$.

B. Temperature Sensor

Since the propagation of a SAW transducer is temperature dependent, the temperature can be obtained from the phase shift of the reflected signal. The total phase shift of the reflected signal relative to the input signal is given by $$\phi = \omega t_d + \phi_{IDT} + \phi_i, \quad (2)$$

where $\omega t_d = 2\pi f L/v$ corresponds to the phase shift introduced by the delay time $t_d$, when a SAW propagates along a delay line L at a velocity v. f is the resonant frequency of the IDT, $\phi_{IDT}$ and $\phi_i$ are the phase shifts introduced by the reflector IDT and impedance load. In case of SAW$_2$, $\phi_{IDT}$ and $\phi_i$ are independent of the temperature. The only temperature dependent parameters are L and v. Therefore, the phase shift over the temperature change can be expressed as $$\frac{d\phi}{dT} = \omega \frac{dt_d}{dT} = \omega t_d \left(\frac{1}{L}\frac{dL}{dT} - \frac{1}{v}\frac{dv}{dT}\right), \quad (3)$$

where $$\left(\frac{1}{L}\frac{dL}{dT} - \frac{1}{v}\frac{dv}{dT}\right)$$

is defined as TCD (temperature coefficient of delay), which represents the increment of the delay time over a temperature increase. TCD is attributed to both the thermal expansion of the delay length and the change of the acoustic velocity due to a temperature change.

With a given value for the TCD, the phase shift for a temperature change ΔT can be expressed as $$\Delta\phi = \omega t_d \text{TCD} \cdot \Delta T \quad (4)$$

$S_t = -\text{phase}(SAW_2)$ is recorded as a representation of the temperature.

C. Humidity Sensor

Temperature is not the only factor that can change the SAW velocity. In general, SAW velocity depends on a number of material properties and surface conditions, which include conductivity, permittivity, viscosity and mass loading, etc. SAW-based humidity sensors commonly use coating layers on the SAW path to absorb water molecules and induce a SAW velocity change. The velocity change can be converted to the phase shift in the same way as in the case of SAW temperature sensors. In this work, an exemplary hydrogel polymer is Aquasonic ultrasound transmission gel used as the coating layer in order to change the phase of $SAW_1$ through humidity. Since path $P_1$ is affected by both the humidity and the temperature, the phase shift caused by temperature changes has to be removed from phase ($SAW_1$) using the temperature information gathered from phase ($SAW_2$). By taking into account the delay length difference $L_1$ and $L_2$, the humidity signal can be found as $$S_h = \text{phase}\left(SAW_1 - \frac{L_1}{L_2}SAW_2\right)(deg) \quad (5)$$

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Fabrication

In an exemplary embodiment, the sensor can be fabricated on a 4", 500 μm thick, 128° Y-X cut $LiNbO_3$ wafer, which has a large TCD of 75 ppm/° C. and a high electromagnetic coupling coefficient of 5.5%. The fabrication of the device may start with the metalization of the IDTs. A 10 nm Ti adhesion layer and a 150 nm Au layer are deposited on the $LiNbO_3$ substrate using a dc magnetron sputter. SAW structures are patterned using photolithography and dry etching. After removing the residual photoresist, using acetone and oxygen plasma, another photolithography step can be processed for patterning of the GMI sensor. Layers of 100 nm $Ni_{80}Fe_{20}$, 200 nm Cu and 100 nm $Ni_{80}Fe_{20}$ are e-beam evaporated with a constant magnetic field of 200 Oe applied in-plane and perpendicular to the designed current flow direction of the GMI sensor. After lift-off, the fabrication of the magnetic and temperature sensing components can be completed.

For the fabrication of the humidity sensing component, 5 mg of hydrogel can be dissolved in 1 ml deionized water. A micropipette may be used to spread a 3 μl solution on the area between $s_1$ and $r_1$. After that, the sample is baked on a hot plate at 60° C. for 20 min to dehydrate the coating. For the last step, a 5×10×1.3 mm PDMS cavity is fabricated through soft lithography and, then, mounted on the sensor to protect the $P_2$ from humidity.

FIG. 3(a) shows the fabricated sensor. The GMI element, FIG. 3(b), has a meander structure with l=2000 μm and w=80 μm. The size of the fabricated sensor chip is 10×10×2 mm. After the fabrication, the sensor is wire bonded to a PCB with a SMA port for the measurement connection.

Experimental Setup

The sensor is tested for changing environmental conditions, i.e. humidity, temperature and magnetic field. Instead of interrogating the sensor via antennas, an Agilent E8363C network analyzer is directly connected to the sensor using an RF cable. The time domain waveform of $S_{11}$ is obtained through the inverse Fourier Transform from the frequency spectrum. For the humidity measurement, samples with different relative humidities are prepared using saturated salt solutions, which include LiCl (11%), $CH_3CO_2K$ (23%), $Mg(NO_3)_2$ (52%), NaCl (75%) and KCl (86% RH). The samples are stored in 20 ml bottles. The measurements are carried out by placing the senor into one bottle after the other at about 5 mm above the solution. Each sample bottle is sealed with a cover to create a saturated vapor environment. For the temperature measurement, in a 24° C. laboratory environment, a 35° C. constant temperature heat source is connected and disconnected to the sensor every 2 mins. For the magnetic field measurement, the sample is placed in a uniform magnetic field at the center of a Helmholtz coil. The field strength is controlled by the current applied to the coil with a power supply. In the above measurements, although the measurands are changed one by one, all three types of data $S_m$, $S_t$ and $S_h$ are recorded at the same time.

Measurement and Discussion

Figure 4A:
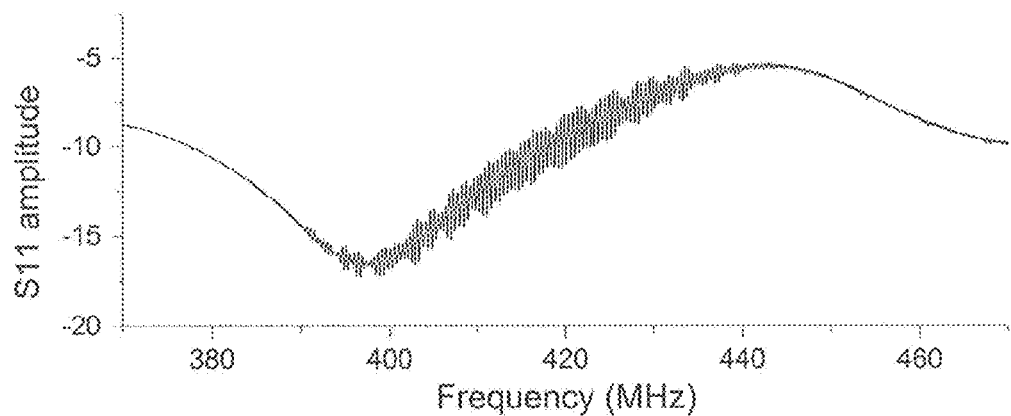
FIG. 4(a) depicts an exemplary frequency domain signal of $S_{11}$.
Figure 4B:
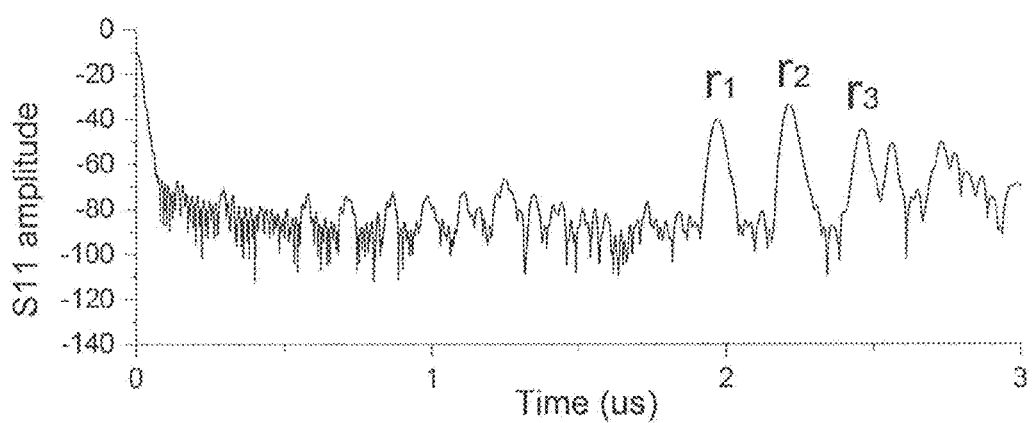
FIG. 4(b) depicts the amplitude of $S_{11}$ in the time domain.

The SAW is normally measured in pulsed interrogation mode through a wireless transceiver or continuous wave mode through a network analyzer with wire connection. In this experiment, a network analyzer is used to read the amplitude and phase data of the device. The resonance frequency of the sensor is around 420 MHz with a bandwidth of 40 MHz. The frequency domain signal of is shown in FIG. 4(a). The time domain signal of the $S_{11}$ amplitude, obtained by the inverse Fourier transform, is shown in FIG. 4(b). Three reflection signals reflected by $r_1$, $r_2$ and $r_3$ are observed at 2 μs, 2.25 μs and 2.5 μs which correspond to $SAW_1$, $SAW_2$ and $SAW_3$. In the experiment, by reading the amplitude and phase data at these three time points, $S_m$, $S_t$ and $S_h$ can be obtained.

Figure 5:
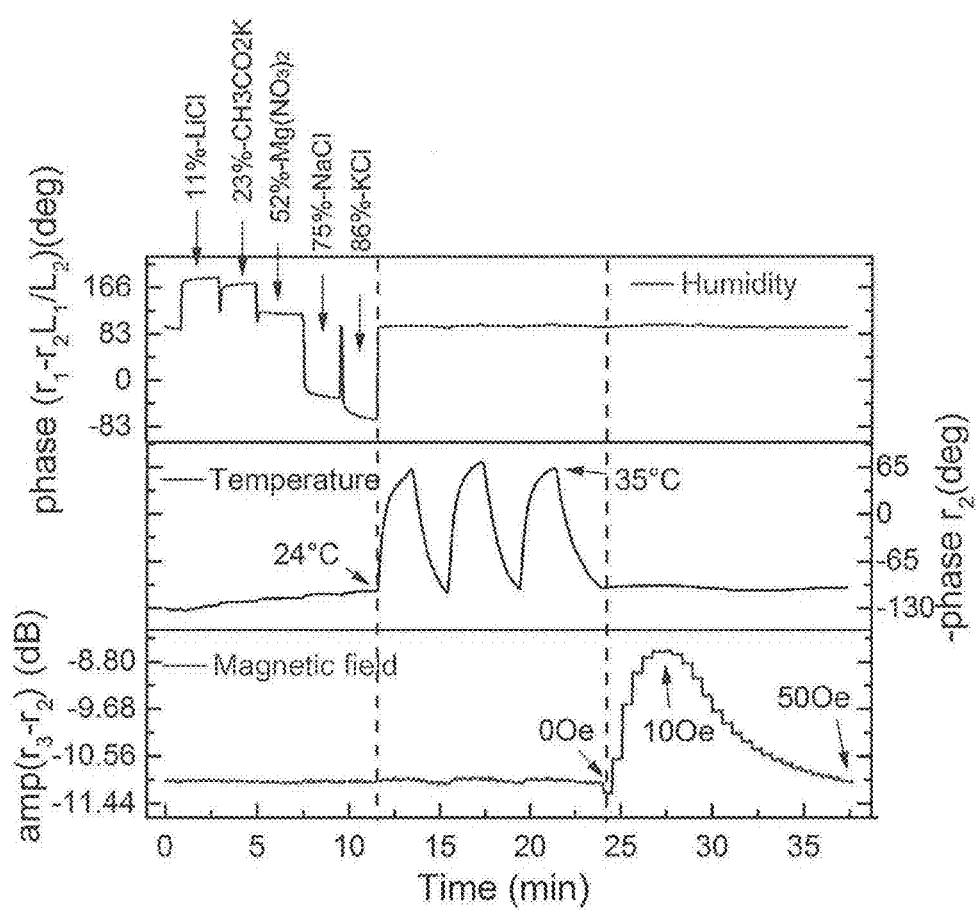
FIG. 5 depicts an exemplary experimental multi-channel measurement of the sensing parameters humidity, temperature and magnetic field.

FIG. 5 shows the experimental result obtained from testing all three sensing parameters. In $S_h$ a 249° phase shift is observed with a humidity change from 11% to 86%. The spike signals between different humidity levels are due to the sensor's exposure to the laboratory environment, when changing the samples. For the high humidity samples NaCl and KCl, it takes more than 2 minutes to reach the saturation equilibrium. In the experiment, an increase of $S_t$ is also observed, which we attribute to the temperature increase due to the heat generated during condensation. In case of the temperature measurement, for an 11° C. temperature change, a 163° phase shift of $S_t$ is observed with no interference with $S_h$. The temperature changes cause small fluctuations of $S_m$. Although the temperature increase mainly causes a phase shift of the reflected signal, it also results in a larger damping [4, 12]. As $S_m$ is extracted based on the amplitude value of the fixed points on the delay line, the amplitude change caused by the shift of the reflection signal is not fully compensated through amp($SAW_3$–$SAW_2$), due to the differences of the reflection signals $r_2$ and $r_3$ in size and position. A more accurate expression for $S_m$ needs to be derived taking into account both the temperature effect and transmission loss. For the magnetic field measurement, an increasing magnetic field from 0-50 Oe is applied with a step of 2 Oe. The result shows a typical nonlinear GMI response with a 2.6 dB change of $S_m$. No interference of the magnetic field is found with $S_h$ and $S_t$.

Figure 6:
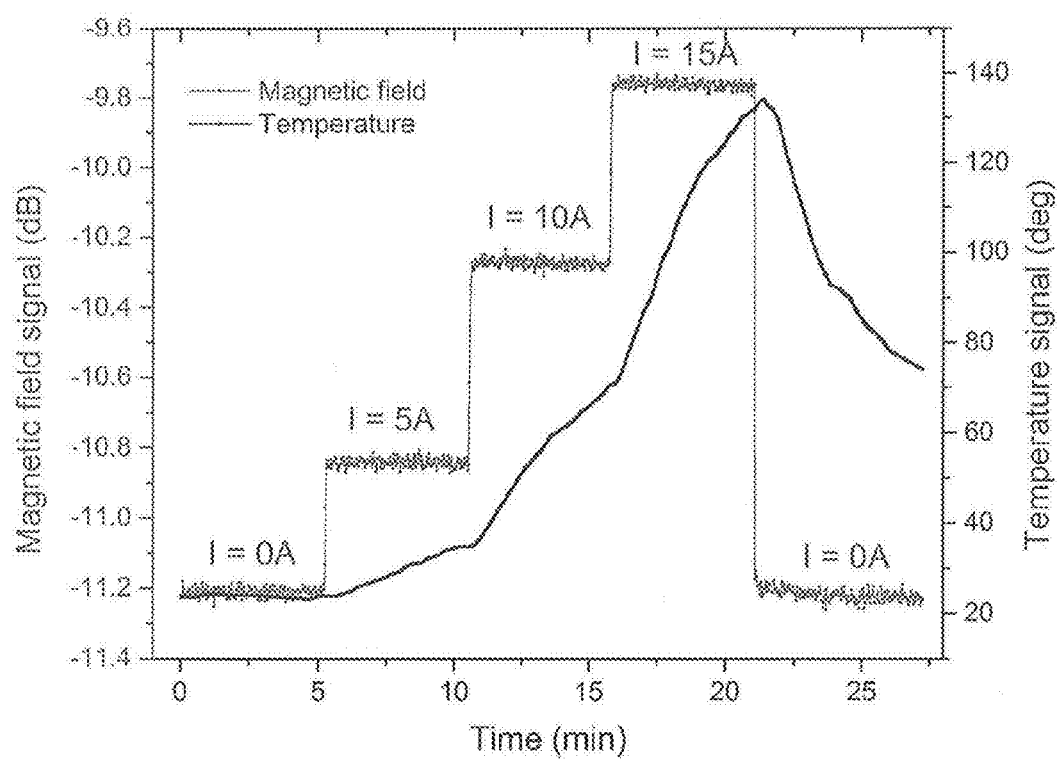
FIG. 6 depicts measured magnetic field produced by the current, and the increase of the wire temperature due to resistive losses.

FIG. 6 depicts a magnetic field and temperature measurement on a 2 mm diameter copper wire carrying a dc current with a 5 A step change applied.

We have, thus, demonstrated, a new type of SAW-based multifunctional passive wireless sensor designed and fabricated for simultaneous measurement of one or more of magnetic field, temperature and humidity. The multi-sensing capabilities and passive wireless features are attractive for high voltage transmission line monitoring. As an example, the sensor size can be 10×10×2 mm, which is much smaller than the conventional solution. Multiple sensing mechanisms can be integrated in a single chip.

Advantages of the present sensor include its magnetic field sensing component (IDT+magnetic field sensitive load): for example usage of strip and meander structured multilayer thin films as a magnetic sensitive impedance load for IDT. The thin film can be fabricated using the standard micro-fabrication technology. Usage of thin film type magneto-impedance load improves the sensor's integrity. In addition, by designing the film thickness and geometry, the sensitivity and operation frequency of the magneto-impedance load can be tailored to match the IDT with different working frequencies. The meander structure can thus provide a greater impedance value with a smaller sensor size, resulting in a higher impedance dynamic range and a stronger signal.

Another advantage is the usage of on-chip matching components for the load impedance matching between the magnetic sensitive impedance load and IDT. On-chip matching improves the sensor's integrity and avoids the external matching component. The external matching introduces extra bonding which affects the matching stability device reproducibility.

The integration of magnetic field, temperature and humidity sensing components and the data extraction from one common interrogation signal provides yet another advantage. Both the amplitude and phase signals of the delay line can be utilized at the same time. This is unexpected, since temperature and humidity interfere with the magnetic field measurement and with each other. Further, one IDT can be used for the temperature sensing. The same IDT can also be used as a phase reference for humidity sensing and amplitude reference for magnetic field sensing. Dual SAW paths can be used to separate the humidity sensing function area and magnetic field/temperature sensing function area. A humidity sealing layer can be applied to the magnetic field/temperature sensing function area to avoid signal damping under the condition of condensation. It makes the device more durable and capable of measuring the temperature and magnetic field data in an extremely humid environment.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

REFERENCES

[1] A. Pohl, "A review of wireless SAW sensors," *Ultrasonics, Ferroelectrics and Frequency Control, IEEE Transactions on*, vol. 47, pp. 317-332, 2000.

[2] L. M. Reindl, A. Pohl, G. Scholl, and R. Weigel, "SAW-based radio sensor systems," *IEEE Sensors Journal*, vol. 1, pp. 69-78, 2001.

[3] L. M. Reindl, "Wireless Passive Sensors: Basic Principles and Performances," in *IEEE SENSORS 2008 Conference*, Lecce, pp. 1607-1610.

[4] A. Binder and R. Fachberger, "Wireless SAW Temperature Sensor System for High-Speed High-Voltage Motors," *IEEE SENSORS JOURNAL*, vol. 11, p. 5, 2011.

[5] C. Lim, W. Wang, S. Yang, and K. Lee, "Development of SAW-based multi-gas sensor for simultaneous detection of CO2 and NO2," *Sensors and Actuators B: Chemical*, vol. 154, pp. 9-16, 2011.

[6] J. M. Friedt, T. Rétornaz, S. Alzuaga, T. Baron, G. Martin, T. Laroche, et al., "Surface acoustic wave devices as passive buried sensors," *Journal of Applied Physics*, vol. 109, p. 034905, 2011.

[7] F. V. B. de Nazaré and M. M. Werneck, "Hybrid optoelectronic sensor for current and temperature monitoring in overhead transmission lines," *Sensors Journal, IEEE*, vol. 12, pp. 1193-1194, 2012.
[8] M.-H. Phan and H.-X. Peng, "Giant magnetoimpedance materials: Fundamentals and applications," *Progress in Materials Science*, vol. 53, pp. 323-420, 2008.
[9] L. Chen, Y. Zhou, C. Lei, and Z.-M. Zhou, "Giant magnetoimpedance effect and voltage response in meander shape Co-based ribbon," *Applied Physics A*, vol. 98, pp. 861-865, 2010.
[10] L. Reindl and W. Ruile, "Programmable Reflectors for SAW-ID-Tags.," in *Proc. IEEE Ultrason. Symp*, Baltimore, 1993, pp. 125-130.
[11] B. Li and J. Kosel, "A Thin film passive magnetic field sensor operated at 425 MHz," in *Solid-State Sensors, Actuators and Microsystems Conference (TRANSDUCERS)*, 2013 17th International, 2013.
[12] R. Fachberger, G. Bruckner, G. Knoll, R. Hauser, J. Biniasch, and L. Reindl, "Applicability of LiNbO3, Langasite and GaPO4 in High Temperature SAW Sensors Operating at Radio Frequencies," *IEEE Trans Ultrason Ferroelectr Freq Control*, vol. 51, p. 4, 2004.
[13] http://www.eng.morgan.edu/~cibac/events/Day2/IVHM/2-Passive%20Wireless%20SAW%20Sensors%20(Wilson).pdf
[14] http://link.springer.com/chapter/10.1007%2F978-3-662-07322-3_8#

The invention claimed is:

1. A sensor apparatus comprising:
at least one input transducer for receiving a signal and generating surface acoustic waves from the signal;
a first surface acoustic wave propagation path for receiving a first surface acoustic wave from the at least one input transducer, the first surface acoustic wave propagation path including a first reflector transducer coupled with or operating as a first sensor; and
a second surface acoustic wave propagation path for receiving a second surface acoustic wave from the at least one input transducer, the second surface acoustic wave propagation path including a second reflector transducer operating as a second sensor and coupled with a third sensor,
wherein the first and second sensors are selected from the group consisting of a humidity sensor a temperature sensor, and combinations thereof,
wherein the third sensor includes a magnetic field sensor that is a magneto-impedance sensor.

2. The sensor apparatus of claim 1, wherein a phase shift or an amplitude change or both are obtained in a surface acoustic wave generated by the at least one input transducer on a reflection of the surface acoustic wave by at least one reflector transducer in the first and second surface acoustic wave propagation paths.

3. The sensor apparatus of claim 1, wherein the at least one input transducer comprises an inter-digital transducer.

4. The sensor apparatus of claim 1, further including a piezoelectric substrate.

5. The sensor apparatus of claim 1, wherein the magnetic field sensor changes impedance upon changes of a magnetic field, changing the surface acoustic wave reflected by its associated reflector transducer.

6. The sensor apparatus of claim 1, wherein the first sensor includes a humidity sensor that is a delay line coupling the at least one input transducer and a reflector transducer, the delay line coated with a humidity sensitive film.

7. The sensor apparatus of claim 1, further including a thermally sensitive substrate.

8. The sensor apparatus of claim 1, the sensor apparatus being a single component.

9. A system comprised of the sensor apparatus of claim 1, a transceiver and one or more antennas.

10. The sensor apparatus of claim 1, wherein a resonant frequency of the first sensor in the first surface acoustic wave propagation path is the same as resonant frequencies of the second reflector transducer and the third sensor in the second surface acoustic wave propagation path.

11. A sensor apparatus comprising:
at least one input transducer for receiving a signal and generating surface acoustic waves from the signal;
a first surface acoustic wave propagation path for receiving a first surface acoustic wave from the at least one input transducer, the first surface acoustic wave propagation path including a first reflector transducer coupled with or operating as a first sensor; and
a second surface acoustic wave propagation path for receiving a second surface acoustic wave from the at least one input transducer, the second surface acoustic wave propagation path including a second reflector transducer operating as a second sensor and coupled with a third sensor,
wherein the first sensor comprises a humidity sensor and the third sensor comprises a magnetic field sensor,
wherein the second reflector transducer operates as a temperature sensor and is coupled with the magnetic field sensor, the first and second surface acoustic wave propagation paths being protected against influencing each other.

12. A method of sensing a change in one or more measurands, comprising the steps of:
receiving a signal and generating surface acoustic waves from the signal;
propagating a surface acoustic wave along a first surface acoustic wave propagation path and a second surface acoustic wave propagation path, the first surface acoustic wave propagation path including a first reflector transducer coupled with or operating as a first sensor, the second surface acoustic wave propagation path including a second reflector transducer operating as a second sensor and coupled with a third sensor, wherein the first and second sensors are selected from the group consisting of a humidity sensor, a temperature sensor, and combinations thereof;
reflecting the surface acoustic wave propagated along the first surface acoustic wave propagation path;
reflecting the surface acoustic wave propagated along the second surface acoustic wave propagation path; and
determining a phase shift or an amplitude change or both between the surface acoustic wave reflected in the first surface acoustic wave propagation path and the surface acoustic wave reflected in the second surface acoustic wave propagation path thereby sensing a change in at least one of humidly, magnetic field or temperature as a measurand,
wherein the third sensor includes a magnetic field sensor that changes impedance upon changes of a magnetic field, causing a phase shift or an amplitude change or both of a surface wave reflected by its associated second reflector transducer.

13. The method of claim 12, wherein the signal is received by an input inter-digital transducer that generates the surface acoustic waves from the signal.

14. The method of claim 12, wherein the first and second surface acoustic wave propagation paths are provided on a piezoelectric substrate.

15. The method of claim 12, wherein the signal is received by an input transducer that generates the surface acoustic wave from the signal, wherein the first sensor includes a humidity sensor that is a delay line coupling the input transducer and the first reflector transducer coupled with the humidity sensor, the delay line coated with a humidity sensitive hydrogel.

16. The method of claim 12, wherein the first and second surface acoustic wave propagation paths are formed on a thermally sensitive substrate.

17. The method of claim 12, wherein a resonant frequency of the first sensor in the first surface acoustic wave propagation path is the same as resonant frequencies of the second reflector transducer and the third sensor in the second surface acoustic wave propagation path.

18. A method of sensing a change in one or more measurands, comprising the steps of:
receiving a signal and generating surface acoustic waves from the signal;
propagating a surface acoustic wave along a first surface acoustic wave propagation path and a second surface acoustic wave propagation path, the first surface acoustic wave propagation path including a first reflector transducer coupled with or operating as a first sensor, the second surface acoustic wave propagation path including a second reflector transducer operating as a second sensor and coupled with a third sensor, wherein the first sensor comprises a humidity sensor, the second sensor comprises a temperature sensor, and the third sensor comprises a magnetic field sensor;
reflecting the surface acoustic waves propagated along the first and second surface acoustic wave propagation paths;
protecting the first and second surface acoustic wave propagation paths against influencing each other; and
determining a phase shift or an amplitude change or both between the surface acoustic wave reflected in the first surface acoustic wave propagation path and the surface acoustic wave reflected in the second surface acoustic wave propagation path thereby sensing a change in at least one of humidly, magnetic field or temperature as a measurand.

* * * * *